(12) United States Patent
Takahashi et al.

(10) Patent No.: US 10,973,708 B2
(45) Date of Patent: Apr. 13, 2021

(54) ABSORBENT PRODUCT

(71) Applicant: LIVEDO CORPORATION, Shikokuchuo (JP)

(72) Inventors: Yuki Takahashi, Tokushima (JP);
Miyuki Fujimoto, Tokushima (JP);
Hironobu Yokokawa, Tokushima (JP);
Osamu Moriura, Tokushima (JP);
Kazuya Maruhata, Tokushima (JP)

(73) Assignee: LIVEDO CORPORATION, Shikokuchuo (JP)

( * ) Notice: Subject to any disclaimer, the term of this patent is extended or adjusted under 35 U.S.C. 154(b) by 295 days.

(21) Appl. No.: 15/776,963

(22) PCT Filed: Oct. 21, 2016

(86) PCT No.: PCT/JP2016/081331
§ 371 (c)(1),
(2) Date: May 17, 2018

(87) PCT Pub. No.: WO2017/098819
PCT Pub. Date: Jun. 15, 2017

(65) Prior Publication Data
US 2018/0344542 A1     Dec. 6, 2018

(30) Foreign Application Priority Data

Dec. 9, 2015  (JP) ................................ 2015-239966
Dec. 9, 2015  (JP) ............................. JP2015-239965

(51) Int. Cl.
*A61F 13/15*     (2006.01)
*A61F 13/539*    (2006.01)
(Continued)

(52) U.S. Cl.
CPC ...... *A61F 13/539* (2013.01); *A61F 13/15731* (2013.01); *A61F 13/47* (2013.01);
(Continued)

(58) Field of Classification Search
CPC .. A61F 13/539; A61F 13/15731; A61F 13/47; A61F 13/505; A61F 13/515;
(Continued)

(56) References Cited

U.S. PATENT DOCUMENTS 4,251,643 A   2/1981  Harada et al.
4,988,344 A   1/1991  Reising et al.
(Continued)

FOREIGN PATENT DOCUMENTS

CN       204072509 U    1/2015
EP       1 419 755 A1   5/2004
(Continued)

OTHER PUBLICATIONS

Notification Concerning Transmittal of International Preliminary Report on Patentability (Form PCT/IB/326) issued in counterpart International Application No. PCT/JP2016/081331 dated Jun. 21, 2018, with Forms PCT/IB/373, PCT/IB/338, and PCT/ISA/237. (16 pages).

(Continued)

*Primary Examiner* — Jacqueline F Stephens
(74) *Attorney, Agent, or Firm* — Westerman, Hattori, Daniels & Adrian, LLP (57) ABSTRACT

In an absorbent product (1), a first absorbent sheet (22) is disposed between a top sheet (21) and a back sheet (23). A second absorbent sheet (22*a*) is disposed between the first absorbent sheet (22) and the back sheet (23). The first absorbent sheet (22) includes a first upper sheet (221), a first highly absorbent material (222), and a first lower sheet (223). The first absorbent sheet (22) extends in the longitudinal direction beyond the longitudinal edges of the second absorbent sheet (22*a*) on both longitudinal sides. On each longitudinal side, an extension (224) of the first absorbent sheet (22) beyond the second absorbent sheet (22*a*) includes (Continued)

a back-sheet contact region (225) that is spaced in the longitudinal direction from the longitudinal edge of the second absorbent sheet (22a) and that is in contact with the back sheet (23). This configuration suppresses the return of liquid.

10 Claims, 6 Drawing Sheets

(51) Int. Cl.
*A61F 13/505* (2006.01)
*A61F 13/47* (2006.01)
*A61F 13/515* (2006.01)
*A61F 13/51* (2006.01)
*A61F 13/53* (2006.01)

(52) U.S. Cl.
CPC .......... *A61F 13/505* (2013.01); *A61F 13/515* (2013.01); *A61F 2013/5103* (2013.01); *A61F 2013/51033* (2013.01); *A61F 2013/530481* (2013.01)

(58) Field of Classification Search
CPC .... A61F 2013/5103; A61F 2013/51033; A61F 2013/530481
USPC .............................. 604/385, 101, 378, 385.01
See application file for complete search history.

(56) References Cited

U.S. PATENT DOCUMENTS

| | | | |
|---|---|---|---|
| 6,011,195 A * | 1/2000 | Muhs | A61F 13/15203 604/367 |
| 6,562,168 B1 | 5/2003 | Schmitt et al. | |
| 6,610,899 B1 | 8/2003 | Divo et al. | |
| 6,642,430 B1 | 11/2003 | Busam et al. | |
| 2001/0014797 A1 | 8/2001 | Suzuki et al. | |
| 2002/0133132 A1 | 9/2002 | Copat et al. | |
| 2012/0232508 A1* | 9/2012 | Urushihara | A61F 13/539 604/365 |
| 2013/0035656 A1 | 2/2013 | Moriya et al. | |
| 2014/0128828 A1 | 5/2014 | Andersson et al. | |
| 2015/0173971 A1 | 6/2015 | Johansson et al. | |
| 2017/0135869 A1 | 5/2017 | Moriya et al. | |

FOREIGN PATENT DOCUMENTS

| | | |
|---|---|---|
| JP | 61-59141 A | 9/1979 |
| JP | H06-031722 U | 4/1994 |
| JP | 2907867 A | 6/1999 |
| JP | 2001-190581 A | 7/2001 |
| JP | 2002-513635 A | 5/2002 |
| JP | 2002-519146 A | 7/2002 |
| JP | 2002-541979 A | 12/2002 |
| JP | 2003-116917 A | 4/2003 |
| JP | 2011-136078 A | 7/2011 |
| JP | 2014-518131 A | 7/2014 |
| JP | 2014-193207 A | 10/2014 |
| JP | 5669976 B1 | 2/2015 |
| JP | 2015-519154 A | 7/2015 |
| JP | 2016-7340 A | 1/2016 |
| WO | 2011/105413 A1 | 2/2013 |

OTHER PUBLICATIONS

International Search Report dated Dec. 27, 2016, issued in Counterpart of International Application No. PCT/JP2016/081331 (2 pages).

Extended (Supplementary) European Search Report dated Apr. 24, 2019, issued in counterpart EP application 16872719.6. (8 pages).

Office Action dated Dec. 2, 2019, issued in counterpart JP Application No. 2015-239966, with English translation. (15 pages).

Office Action dated Jun. 15, 2020, issued in counterpart CN Application No. 201680073935.X, with English translation (20 pages).

\* cited by examiner

ABSORBENT PRODUCT

TECHNICAL FIELD

The present invention relates to an absorbent product for receiving body wastes from a wearer.

BACKGROUND ART

Absorbent products such as an absorbent pad for light incontinence that is used by being attached to the inner side of a disposable diaper conventionally use an absorbent sheet as an absorber disposed between the top sheet and the back sheet, the absorbent sheet being produced by sandwiching and fixing particles of a highly absorbent resin or the like between two sheet members such as nonwoven fabric, as described in Japanese Translations of PCT Applications No. 2002-541979 (Document 1), No. 2002-513635 (Document 2), and No. 2002-519146 (Document 3). The absorbent sheet is formed by, for example, continuously supplying particles of a highly absorbent resin or the like on a long sheet member, superimposing another long sheet member from above on the particles, and bonding side edge portions of the two sheet members before cutting the sheet members to a predetermined length.

Document 1 discloses a technique for suppressing the escape of particles such as a highly absorbent resin to the outside from the longitudinal ends of the absorbent sheets by applying a foaming agent to cut portions (i.e., the longitudinal ends of the absorbent sheets) from above one of the sheet members after the two sheet members are cut. Document 2 proposes a technique in which the two sheet members are cut after a superabsorbent material movement obstruction agent is applied to to-be-cut portions of the two sheet members from above one of the sheet members. Document 3 proposes a technique in which the cutting of the two sheet members and the application of a superabsorbent material movement obstruction agent to the cut portions are carried out simultaneously. Japanese Patent Application Laid-Open No. 2014-193207 (Document 4) uses, for example, a thermoplastic polymer having a softening point in the range of 50 to 300° C. as a superabsorbent material movement obstruction agent.

According to Document 4, the absorber between the top sheet and the back sheet may be fiber stacking of pulp fibers, an aggregate of filaments such as cellulose acetate, or a nonwoven fabric that may be mixed with or fixed to a highly absorbent polymer as necessary. This absorber is formed by laminating upper and lower layers. The ends of the upper layer of the absorber extend outward beyond the lower layer, and these extensions are turned toward the back sheet.

In the case of manufacturing an absorbent sheet as described above, if the blowing agent or the superabsorbent material movement obstruction agent is applied from above one of the sheet members as in Documents 1 to 3, the blowing agent or the superabsorbent material-movement obstruction agent may not be applied sufficiently between the two sheet members. In this case, the adhesion of the two sheet members may become insufficient, and particles of the highly absorbent resin may escape from the longitudinal ends of the absorbent sheet. Moreover, it is not easy with the manufacturing method according to Document 1 to apply the foaming agent with high positional accuracy to the longitudinal ends of the cut absorbent sheet. With the manufacturing method according to Document 3, the amount of the superabsorbent material movement obstruction agent applicable at the same time as the cutting of the two sheet members is relatively small, and therefore the adhesion of the two sheet members may become more insufficient.

With the absorber formed by laminating the upper and lower layers as in Document 4, a liquid such as urine that has passed through the upper layer may return to the top sheet as a result of passing through the upper sheet before being absorbed by the lower layer. The return of the liquid may cause the wearer discomfort since the liquid such as urine having returned to the top sheet may adhere to the wearer's skin.

SUMMARY OF INVENTION

The present invention is intended for an absorbent product for receiving body wastes from a wearer, and it is an object of the present invention to suppress the return of liquid.

The absorbent product according to the present invention includes a liquid-pervious top sheet, a water-repellent or liquid-impervious back sheet, a first absorbent sheet disposed between the top sheet and the back sheet, and a second absorbent sheet disposed between the first absorbent sheet and the back sheet. The first absorbent sheet includes a first upper sheet, a first lower sheet disposed between the first upper sheet and the back sheet, and a first highly absorbent material in particulate or fibrous form that is fixed between the first upper sheet and the first lower sheet. The second absorbent sheet includes a second upper sheet, a second lower sheet disposed between the second upper sheet and the back sheet, and a second highly absorbent material in particulate or fibrous form that is fixed between the second upper sheet and the second lower sheet. On each side in a longitudinal direction, the first absorbent sheet extends in the longitudinal direction beyond an edge in the longitudinal direction of the second absorbent sheet, and the extension of the first absorbent sheet beyond the second absorbent sheet includes a back-sheet contact region that is spaced in the longitudinal direction from the edge of the second absorbent sheet and that is in contact with the back sheet. With this absorbent product, it is possible to suppress the return of liquid.

In a preferred embodiment of the present invention, on each side in the longitudinal direction, a distance in the longitudinal direction between the back-sheet contact region of the first absorbent sheet and the edge of the second absorbent sheet is greater than or equal to 2 mm and less than or equal to 20 mm, and a space surrounded by the first absorbent sheet, the second absorbent sheet, and the back sheet is provided between the back-sheet contact region and the edge of the second absorbent sheet.

In another preferred embodiment of the present invention, an amount of liquid absorbed per unit area of the first absorbent sheet is smaller than an amount of liquid absorbed per unit area of the second absorbent sheet.

In another preferred embodiment of the present invention, the second upper sheet and the second lower sheet are not fixed to each other in each edge portion in the longitudinal direction of the second absorbent sheet.

In another preferred embodiment of the present invention, on each side in the longitudinal direction, the back-sheet contact region of the first absorbent sheet is fixed to the back sheet.

In another preferred embodiment of the present invention, the second upper sheet of the second absorbent sheet is fixed to the first lower sheet of the first absorbent sheet.

In another preferred embodiment of the present invention, the first lower sheet is more pervious to liquid than the second lower sheet.

In another preferred embodiment of the present invention, on each side in a width direction, the first absorbent sheet extends in the width direction beyond a side edge in the width direction of the second absorbent sheet, and the extension of the first absorbent sheet beyond the second absorbent sheet includes a lateral back-sheet contact region that is spaced in the width direction from the side edge in the width direction of the second absorbent sheet and that is in contact with the back sheet.

In another preferred embodiment of the present invention, the first upper sheet and the first lower sheet are fixed to each other in each edge portion in the longitudinal direction of the first absorbent sheet. This prevents the highly absorbent material from escaping from the longitudinal ends of the absorbent sheet.

In another preferred embodiment of the present invention, the fixation of the first upper sheet and the first lower sheet is accomplished by embossing.

More preferably, the fixation of the first upper sheet and the first lower sheet is accomplished by embossing that involves heating.

These and other objects, features, aspects and advantages of the present invention will become more apparent from the following detailed description of the present invention when taken in conjunction with the accompanying drawings.

DESCRIPTION OF EMBODIMENTS

Figure 1:
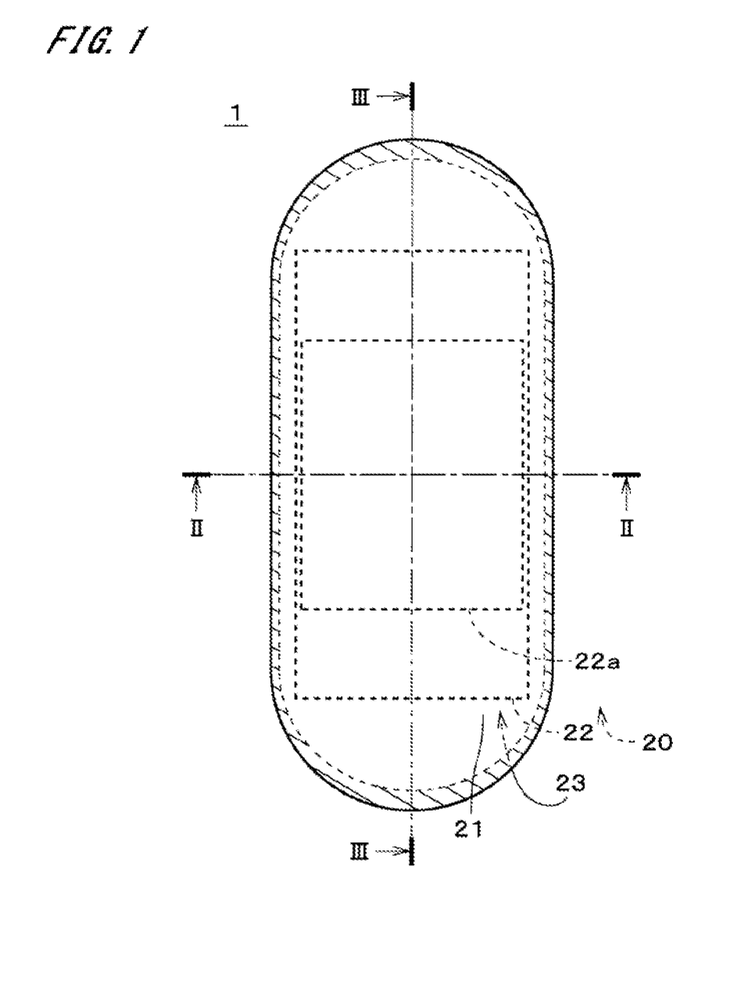
FIG. 1 is a plan view of an absorbent product according to a first embodiment.
Figure 2:
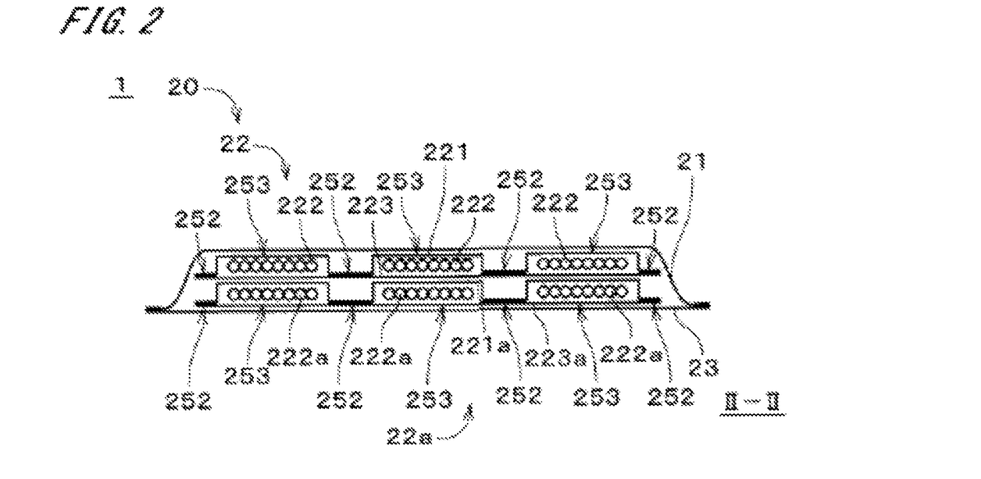
FIG. 2 is a sectional view of the absorbent product.
Figure 3:
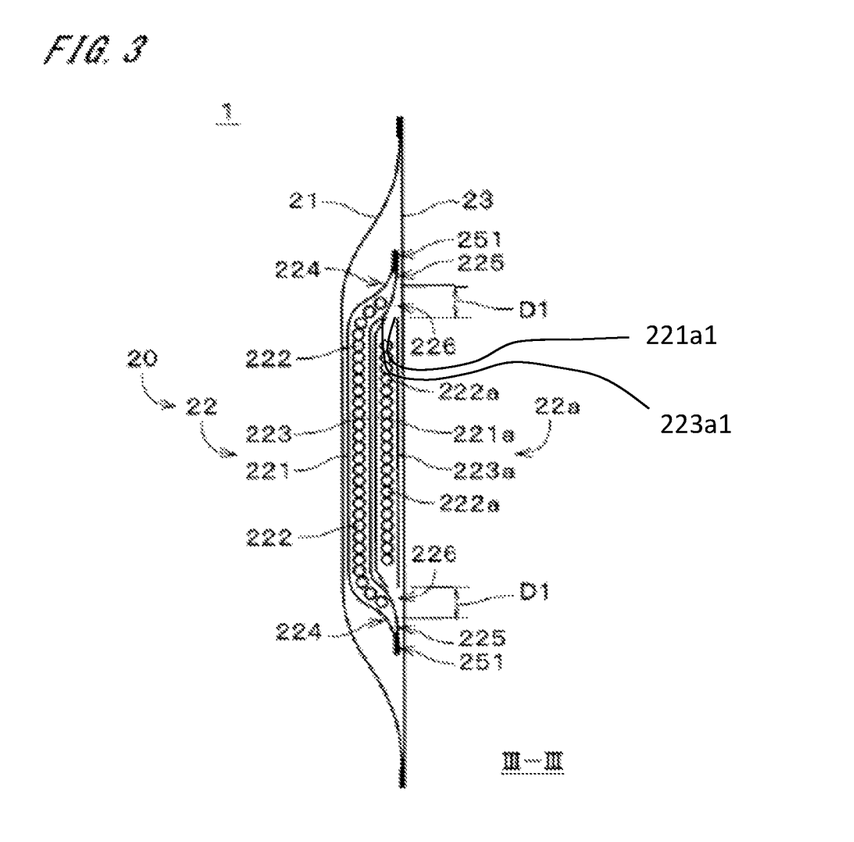
FIG. 3 is a sectional view of the absorbent product.

FIG. 1 is a plan view of an absorbent product 1 according to a first embodiment of the present invention. FIG. 2 is an enlarged view of a section of the absorbent product 1 taken at position II-II in FIG. 1 along a plane perpendicular to the longitudinal direction (i.e., the up-down direction in FIG. 1). FIG. 3 is a sectional view of the absorbent product 1 taken at position III-III in FIG. 1 along a plane perpendicular to the width direction (i.e., the right-left direction in FIG. 1). In FIGS. 2 and 3, the dimension in the up-down direction (i.e., thickness) is illustrated larger than the actual dimension. The same applies to the other sectional views.

The absorbent product 1 receives body wastes from a wearer. The absorbent product 1 may be an absorbent pad for light incontinence that is used by being attached to the inner side of a disposable diaper, which is an exterior product worn by a wearer, and receive liquid wastes such as urine from a wearer. In FIG. 1, the absorbent product 1 is illustrated with its face that comes in contact with a wearer (hereinafter, referred to as "upper face") facing toward the front.

The absorbent product 1 includes a liquid-pervious top sheet 21, a liquid-repellent or liquid-impervious back sheet 23, and an absorber 20 as illustrated in FIGS. 1 to 3. The absorber 20 is a sheet-like member disposed between the top sheet 21 and the back sheet 23. The absorber 20 includes a first absorbent sheet 22 and a second absorbent sheet 22a. The first absorbent sheet 22 and the second absorbent sheet 22a are laminated in the up-down direction. The second absorbent sheet 22a is disposed below the first absorbent sheet 22. In other words, the first absorbent sheet 22 is disposed between the top sheet 21 and the back sheet 23, and the second absorbent sheet 22a is disposed between the first absorbent sheet 22 and the back sheet 23. Approximately the entire lower face of the second absorbent sheet 22a is in contact with the upper face of the back sheet 23. In the example illustrated in FIG. 1, the shapes of the first absorbent sheet 22 and the second absorbent sheet 22a in plan view are generally rectangular shapes whose longitudinal lengths are greater than the crosswise widths.

In order to facilitate comprehension of drawings, the contours of the first absorbent sheet 22 and the second absorbent sheet 22a of the absorber 20 are shown by thick broken lines in FIG. 1. In FIGS. 2 and 3, some components of the absorbent product 1 that in actuality are in contact with one another are shown apart from one another in the up-down direction. In the example illustrated in FIG. 1, the shape of the absorbent product 1 in plan view is a generally oblong shape whose longitudinal length is greater than the crosswise width. The outer edge portion of the top sheet 21 and the outer edge portion of the back sheet 23 are joined throughout the circumference. The joining area of the top sheet 21 and the back sheet 23 is cross-hatched in FIG. 1. In the joining area, the top sheet 21 and the back sheet 23 may adhere to each other with an adhesive or may be press-bonded.

The top sheet 21 is a liquid-pervious sheet material that immediately catches moisture in body wastes received from a wearer and allows the moisture to move to the absorber 20. Examples of the top sheet 21 that can be used include liquid-pervious nonwoven fabrics (e.g., point-bonded nonwoven fabrics, air-through nonwoven fabrics, and spun-bonded nonwoven fabrics) formed of hydrophobic fiber (e.g., polypropylene, polyethylene, polyester, polyamide, or nylon) whose surface has undergone hydrophilic treatment using a surfactant. Examples of the top sheet 21 also include nonwoven fabrics (e.g., spunlace nonwoven fabrics) formed of hydrophilic fiber such as cellulose, rayon, or cotton.

The first absorbent sheet 22 of the absorber 20 includes a first upper sheet 221, a first highly absorbent material 222, and a first lower sheet 223. The first lower sheet 223 is disposed below the first upper sheet 221 and laminated with the first upper sheet 221 in the up-down direction. In other words, the first lower sheet 223 is disposed between the first upper sheet 221 and the back sheet 23.

The first upper sheet 221 and the first lower sheet 223 are liquid-pervious sheet materials. Examples of the first upper sheet 221 and the first lower sheet 223 that can be used include liquid-pervious nonwoven fabrics (e.g., spunlace nonwoven fabrics, air-through nonwoven fabrics, and spun-bonded nonwoven fabrics). For example, the first upper sheet 221 and the first lower sheet 223 may respectively be a spunlace nonwoven fabric and an air-through nonwoven fabric. Alternatively, both the first upper sheet 221 and the first lower sheet 223 may be an air-through nonwoven fabric or a spun-bonded nonwoven fabric. A combination of the materials for the first upper sheet 221 and the first lower sheet 223 may be changed in various ways. The first upper sheet 221 may be more pervious to liquids than the first lower sheet 223. The liquid perviousness may be obtained by the amount of liquid that passes through a unit area of sheet per unit time. The same applies to the following description.

The first highly absorbent material 222 may be a superabsorbent polymer (SAP) in particulate form or a superabsorbent fiber (SAF) in fibrous form. In the example illustrated in FIGS. 2 and 3, the first highly absorbent material 222 is an SAP. In FIGS. 2 and 3, particles of the first highly absorbent material 222 are shown larger than their actual sizes. The first highly absorbent material 222 is fixed between the first upper sheet 221 and the first lower sheet 223. The first absorbent sheet 22 absorbs and retains a liquid having passed through the top sheet 21. Specifically, the first highly absorbent material 222 of the first absorbent sheet 22 absorbs the liquid and swells so that the liquid is contained in the first absorbent sheet 22. In the first absorbent sheet 22, there is substantially no bulky absorbent material (e.g., pulp fiber) other than the first highly absorbent material 222 between the first upper sheet 221 and the first lower sheet 223.

The second absorbent sheet 22a includes a second upper sheet 221a, a second highly absorbent material 222a, and a second lower sheet 223a. The second lower sheet 223a is disposed below the second upper sheet 221a and laminated with the second upper sheet 221a in the up-down direction. In other words, the second lower sheet 223a is disposed between the second upper sheet 221a and the back sheet 23.

The second upper sheet 221a and the second lower sheet 223a are liquid-pervious sheet materials. Examples of the second upper sheet 221a and the second lower sheet 223a that can be used include liquid-pervious nonwoven fabrics (e.g., spunlace nonwoven fabrics, air-through nonwoven fabrics, and spun-bonded nonwoven fabrics). For example, the second upper sheet 221a and the second lower sheet 223a may respectively be a spunlace nonwoven fabric and an air-through nonwoven fabric. Alternatively, both the second upper sheet 221a and the second lower sheet 223a may be an air-through nonwoven fabric or a spun-bonded nonwoven fabric. A combination of the materials for the second upper sheet 221a and the second lower sheet 223a may be changed in various ways. The second upper sheet 221a may be more pervious to liquids than the second lower sheet 223a. Moreover, the first lower sheet 223 of the first absorbent sheet 22 may be more pervious to liquids than the second lower sheet 223a of the second absorbent sheet 22a.

The second highly absorbent material 222a may be an SAP in particulate form or an SAF in fibrous form. In the example illustrated in FIGS. 2 and 3, the second highly absorbent material 222a is an SAP. In FIGS. 2 and 3, particles of the second highly absorbent material 222a are shown larger than their actual sizes. The second highly absorbent material 222a is fixed between the second upper sheet 221a and the second lower sheet 223a. The second absorbent sheet 22a absorbs and retains a liquid having passed through the top sheet 21 and the first absorbent sheet 22. Specifically, the second highly absorbent material 222a of the second absorbent sheet 22a absorbs the liquid and swells so that the liquid is contained in the second absorbent sheet 22a. In the second absorbent sheet 22a, there is substantially no bulky absorbent material (e.g., pulp fiber) other than the second highly absorbent material 222a between the second upper sheet 221a and the second lower sheet 223a.

The materials for the second upper sheet 221a, the second highly absorbent material 222a, and the second lower sheet 223a may be the same as or respectively different from the materials for the first upper sheet 221, the first highly absorbent material 222, and the first lower sheet 223. The second upper sheet 221a of the second absorbent sheet 22a is fixed to the first lower sheet 223 of the first absorbent sheet 22. The fixation of the second upper sheet 221a and the first lower sheet 223 may be accomplished by bonding with a hot-melt adhesive. In this case, the hot-melt adhesive may preferably be applied to the second upper sheet 221a or the first lower sheet 223 by spiral coating. This reduces the possibility that the adhesive might prevent the liquid from passing from the first absorbent sheet 22 to the second absorbent sheet 22a. The fixation of the second upper sheet 221a and the first lower sheet 223 may be accomplished using other various methods.

The back sheet 23 is a liquid-repellent or liquid-impervious sheet member that prevents moisture in body wastes or the like, having reached the back sheet 23, from oozing out of the absorbent product 1. Examples of the back sheet 23 that can be used include liquid-repellent or liquid-impervious nonwoven fabrics or plastic films and laminated sheets obtained by laminating such nonwoven fabrics and plastic films. Examples of the nonwoven fabrics that can be used as the back sheet 23 include spun-bonded nonwoven fabrics, meltblown nonwoven fabrics, and spun-bonded-meltblown-spun-bonded (SMS) nonwoven fabrics, which are formed of hydrophobic fiber and may be made liquid repellent as necessary. In the case of using a plastic film as the back sheet 23, it is preferable for the plastic film to have moisture permeability (air permeability) from the viewpoint of preventing the absorbent product 1 from becoming stuffy and of improving the comfort of the wearer.

The first absorbent sheet 22 has a greater longitudinal length than the second absorbent sheet 22a. The longitudinal length of the second absorbent sheet 22a may be greater than or equal to 50% and less than or equal to 90% of the longitudinal length of the first absorbent sheet 22. The first absorbent sheet 22 and the second absorbent sheet 22a have approximately the same crosswise width. On each longitudinal side of the first absorbent sheet 22, the first absorbent sheet 22 extends in the longitudinal direction beyond the longitudinal edge of the second absorbent sheet 22a. On each longitudinal side, an extension 224 of the first absorbent sheet 22 beyond the second absorbent sheet 22a includes a back-sheet contact region 225 that is spaced in the longitudinal direction from the longitudinal edge 221a1, 223a1 of the second absorbent sheet 22a and that is in contact with the back sheet 23. In other words, the longitudinal edge of the back-sheet contact region 225 on the side closer to the second absorbent sheet 22a is spaced in the longitudinal direction from the longitudinal edge of the second absorbent sheet 22a. In yet other words, there is a non-contact region where the absorber 20 and the back sheet 23 are not in contact, between the back-sheet contact region 225 of the first absorbent sheet 22 and the longitudinal edge of the second absorbent sheet 22a.

On each longitudinal side of the first absorbent sheet 22, the back-sheet contact region 225 of the first absorbent sheet 22 is fixed to the back sheet 23. The fixation of the back-sheet contact region 225 and the back sheet 23 may be accomplished by bonding with a hot-melt adhesive. The fixation of the back-sheet contact region 225 and the back sheet 23 may be accomplished using various other methods.

On each longitudinal side of the first absorbent sheet 22, a distance D1 in the longitudinal direction between the back-sheet contact region 225 of the first absorbent sheet 22 and the longitudinal edge of the second absorbent sheet 22a may be greater than or equal to 2 mm and less than or equal to 20 mm. There is a space 226 surrounded by the first absorbent sheet 22, the second absorbent sheet 22a, and the back sheet 23 (hereinafter, referred to as a "core end space 226") between the back-sheet contact region 225 and the longitudinal edge of the second absorbent sheet 22a₀. The core end space 226 extends generally linearly in the width direction almost throughout the width of the second absorbent sheet 22a.

Figure 4:
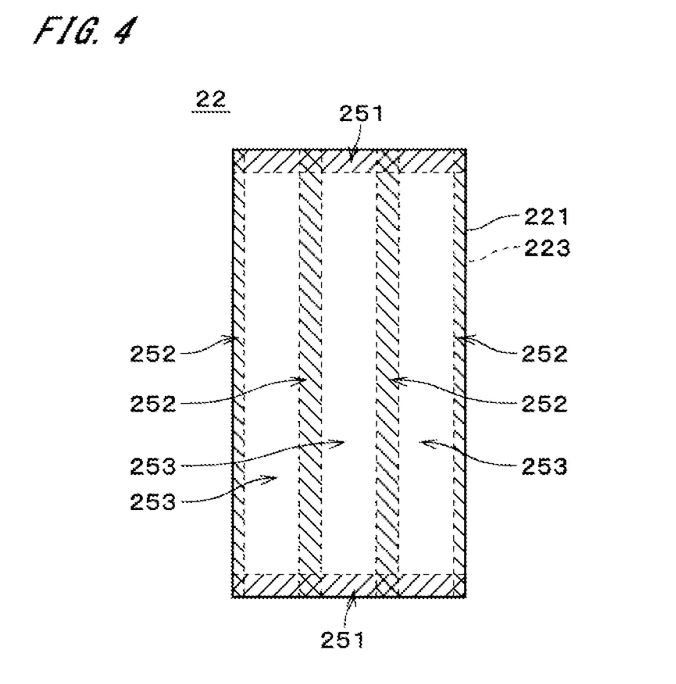
FIG. 4 is a plan view of a first absorbent sheet.

FIG. 4 is a plan view of the first absorbent sheet 22. In FIG. 4, joining areas 251 and 252 where the first upper sheet 221 and the first lower sheet 223 are fixed to each other are cross-hatched. In order to facilitate the distinction between the joining areas 251 and 252, the joining areas 251 and 252 are respectively referred to as "first joining areas 251" and "second joining areas 252" in the following description. As illustrated in FIG. 4, the first absorbent sheet 22 includes two first joining areas 251 and a plurality of (e.g., four) second joining areas 252.

In the example illustrated in FIG. 4, the two first joining areas 251 are located in the longitudinal edge portions of the first absorbent sheet 22. Each first joining area 251 is a generally rectangular area that is along in the width direction of the first absorbent sheet 22. The longitudinal length of each first joining area 251 may be in the range of 5 to 50 mm. Each first joining area 251 is provided almost throughout the crosswise length of the first absorbent sheet 22. In each first joining area 251, the first upper sheet 221 and the first lower sheet 223 are fixed directly to each other. Preferably, the fixation of the first upper sheet 221 and the first lower sheet 223 in the first joining area 251 is accomplished by press bonding. More preferably, the fixation of the first upper sheet 221 and the first lower sheet 223 in the first joining area 251 is accomplished by press bonding by means of embossing. Yet more preferably, the fixation of the first upper sheet 221 and the first lower sheet 223 in the first joining area 251 is accomplished by press bonding by means of embossing that involves heating.

In the case where the press bonding of the first upper sheet 221 and the first lower sheet 223 involves heating, for example, one of the first upper sheet 221 and the first lower sheet 223 may have a higher content of heat-sealing fibers than the other sheet. In the case of manufacturing the first absorbent sheet 22, the first upper sheet 221 and the first lower sheet 223 are press-bonded by pressing this one sheet against the other sheet while heating the one sheet. One example of the aforementioned heat-sealing fiber that can be used is polyethylene with a melting point of approximately 120° C.

In the example illustrated in FIG. 4, the first lower sheet 223 has a higher content of heat-sealing fibers than the first upper sheet 221. When repeatedly receiving a liquid such as urine, nonwoven fabrics with high contents of heat-sealing fibers may become less pervious to liquids than nonwoven fabrics with low contents of heat-sealing fibers. Thus, it is preferable to increase the content of heat-sealing fibers in the first lower sheet 223 rather than increasing the content of heat-sealing fibers in the first upper sheet 221, which is desired to keep exhibiting high liquid-perviousness. Note that the first upper sheet 221 and the first lower sheet 223 may have approximately the same content of heat-sealing fibers.

In the example illustrated in FIG. 4, four second joining areas 252 are aligned and spaced from each other in the width direction of the first absorbent sheet 22. Each second joining area 252 is a generally band-like (i.e., generally rectangular) area that extends linearly in the longitudinal direction of the first absorbent sheet 22. Each second joining area 252 is provided almost throughout the longitudinal length of the first absorbent sheet 22. The four second joining areas 252 are disposed in approximately parallel with each other. The two second joining areas 252 that are located on the opposite outermost sides in the width direction are located in the opposite edge portions in the width direction of the first absorbent sheet 22. In each longitudinal edge portion of the first absorbent sheet 22, the first joining area 251 and the four second joining areas 252 overlap with one another. In FIG. 4, the areas where the first joining areas 251 and the second joining areas 252 overlap are shown with two types of cross hatching.

In the first absorbent sheet 22, the first upper sheet 221 and the first lower sheet 223 are fixed to each other in each of the second joining areas 252. Preferably, the fixation of the first upper sheet 221 and the first lower sheet 223 in the second joining areas 252 is accomplished by press bonding. More preferably, the fixation of the first upper sheet 221 and the first lower sheet 223 in the second joining areas 252 is accomplished by press bonding by means of embossing. Yet more preferably, the press bonding of the first upper sheet 221 and the first lower sheet 223 in the second joining areas 252 is press bonding by means of embossing that involves heating.

As illustrated in FIGS. 2 and 4, a plurality of highly absorbent material fixing parts 253 are disposed among the plurality of second joining areas 252. In each of the highly absorbent material fixing parts 253, the first highly absorbent material 222 is fixed between the first upper sheet 221 and the first lower sheet 223. The plurality of second joining areas 252 and the plurality of highly absorbent material fixing parts 253 are alternately arranged in the width direction of the first absorbent sheet 22. In the example illustrated in FIGS. 2 and 4, three highly absorbent material fixing parts 253 are aligned and spaced from each other in the width direction of the first absorbent sheet 22. The three highly absorbent material fixing parts 253 are disposed in approximately parallel with each other.

Each highly absorbent material fixing part 253 is a generally band-like (i.e., generally rectangular) area that extends linearly in the longitudinal direction of the first absorbent sheet 22. Each highly absorbent material fixing part 253 is provided almost throughout the longitudinal length in the region between the two first joining areas 251 of the first absorbent sheet 22. That is, the plurality of highly absorbent material fixing parts 253 and the plurality of second joining areas 252 are arranged in generally stripe form, and each highly absorbent material fixing part 253 is surrounded by the first joining areas 251 and the second joining areas 252 throughout the periphery. The highly absorbent material fixing parts 253 may have a greater width than the second joining areas 252.

In each highly absorbent material fixing part 253, the first highly absorbent material 222 is fixed to at least one of the first upper sheet 221 and the first lower sheet 223 with an adhesive that is applied to at least one of the upper face of the first lower sheet 223 and the lower face of the first upper sheet 221.

In the process of manufacturing the first absorbent sheet 22, for example, this adhesive may be applied to the entire upper face of the first lower sheet 223 and the entire lower face of the first upper sheet 221. In this case, the adhesive is present between the first upper sheet 221 and the first lower sheet 223 even in the first joining areas 251 and the second joining areas 252. However, the adhesive present between the first upper sheet 221 and the first lower sheet 223 is a small amount and therefore does not contribute much to the fixation of the first upper sheet 221 and the first lower sheet 223. Thus, even in the case where the first joining areas 251 includes the adhesive between the first upper sheet 221 and the first lower sheet 223, the first upper sheet 221 and the first lower sheet 223 are fixed primarily by press bonding as described above. The same applies to the second joining areas 252.

In each second joining area 252, the highly absorbent material 222 is substantially not present between the first upper sheet 221 and the first lower sheet 223. In other words, in each second joining area 252, the first highly absorbent material 222 is not present at all between the first upper sheet 221 and the first lower sheet 223, or it is present in slight density to such an extent that the first highly absorbent material 222 can be regarded as substantially not present, as compared with the first highly absorbent material 222 present in the highly absorbent material fixing parts 253.

If the highly absorbent material fixing parts 253 and the second joining areas 252 described above are respectively referred to as "first regions" and "second regions," a plurality of first regions and a plurality of second regions are alternately arranged in the width direction of the first absorbent sheet 22 in the first absorbent sheet 22. In each of the first regions, the first highly absorbent material 222 is fixed between the first upper sheet 221 and the first lower sheet 223. In the second regions, the first highly absorbent material 222 is not present between the first upper sheet 221 and the first lower sheet 223, and the first upper sheet 221 and the first lower sheet 223 are fixed directly to each other.

In each first joining area 251 described above, the first highly absorbent material 222 is substantially not present between the first upper sheet 221 and the first lower sheet 223 as in the second joining areas 252. In other words, in each first joining area 251, the first highly absorbent material 222 is not present at all between the first upper sheet 221 and the first lower sheet 223, or it is present in slight density to such an extent that the first highly absorbent material 222 can be regarded as substantially not present, as compared with the first highly absorbent material 222 present in the highly absorbent material fixing parts 253. Depending on the method of manufacturing the first absorbent sheet 22, the first joining areas 251 may include the first highly absorbent material 222 at approximately the same density as the first highly absorbent material 222 present in the highly absorbent material fixing parts 253.

Figure 5:
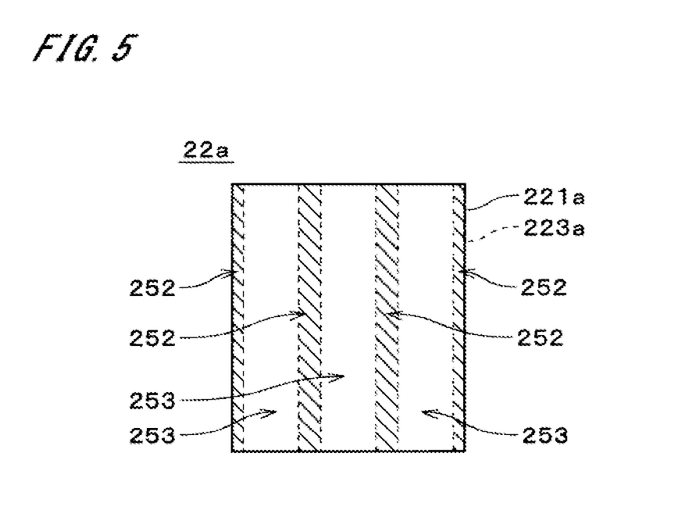
FIG. 5 is a plan view of a second absorbent sheet.

FIG. 5 is a plan view of the second absorbent sheet 22a. The second absorbent sheet 22a has approximately the same structure as the structure of the first absorbent sheet 22, except that the second upper sheet 221a and the second lower sheet 223a are not fixed to each other in the longitudinal edge portions and that the second absorbent sheet 22a has a shorter longitudinal length than the first absorbent sheet 22 as described above. That is, the second absorbent sheet 22a is generally the same as the first absorbent sheet 22 in terms of, for example, the number of second joining areas 252, the number of highly absorbent material fixing parts 253, and the positions and widths in the width direction of the second joining areas 252 and the highly absorbent material fixing parts 253. In FIG. 5, the second joining areas 252 where the second upper sheet 221a and the second lower sheet 223a are fixed to each other are cross-hatched. The joining areas of the second upper sheet 221a and the second lower sheet 223a are also cross-hatched in FIGS. 7 and 10, which will be described later.

In the example illustrated in FIG. 5, the second absorbent sheet 22a includes a plurality of (e.g., four) second joining areas 252. The four second joining areas 252 are aligned and spaced from each other in the width direction of the second absorbent sheet 22a. Each second joining area 252 is a generally band-like (i.e., generally rectangular) area that extends linearly in the longitudinal direction of the second absorbent sheet 22a. Each second joining area 252 is provided almost throughout the longitudinal length of the second absorbent sheet 22a. The four second joining areas 252 are disposed in approximately parallel with each other. The two second joining areas 252 that are located on the opposite outermost sides in the width direction are located in the opposite edge portions in the width direction of the second absorbent sheet 22a.

In the second absorbent sheet 22a, the second upper sheet 221a and the second lower sheet 223a are fixed to each other in each of the second joining areas 252. Preferably, the fixation of the second upper sheet 221a and the second lower sheet 223a in the second joining areas 252 is accomplished by press bonding. More preferably, the fixation of the second upper sheet 221a and the second lower sheet 223a in the second joining areas 252 is accomplished by press bonding by means of embossing. Yet more preferably, the press bonding of the second upper sheet 221a and the second lower sheet 223a in the second joining areas 252 is press bonding by means of embossing that involves heating.

As illustrated in FIG. 5, the longitudinal edge portions of the second absorbent sheet 22a include the ends of the second joining areas 252. That is, in the longitudinal edge portions of the second absorbent sheet 22a, the second upper sheet 221a and the second lower sheet 223a are not fixed to each other, except in the second joining areas 252. In other words, in the longitudinal edge portions of the second absorbent sheet 22a, the second upper sheet 221a and the second lower sheet 223a are not fixed to each other in areas that are adjacent in the longitudinal direction to the highly absorbent material fixing parts 253, which will be described later. Note that the second upper sheet 221a and the second lower sheet 223a may not be fixed to each other throughout the width of the longitudinal edge portions. That is, in the case where the second upper sheet 221a and the second lower sheet 223a are not fixed to each other in the longitudinal edge portions, the second upper sheet 221a and the second lower sheet 223a in the longitudinal edge portions of the second absorbent sheet 22a may not be fixed to each other in the area excluding the second joining areas 252, or may not be fixed to each other throughout the width.

As illustrated in FIGS. 2 and 5, the plurality of highly absorbent material fixing parts 253 are disposed among the plurality of second joining areas 252. In each of the highly absorbent material fixing parts 253, the second highly absorbent material 222a is fixed between the second upper sheet 221a and the second lower sheet 223a. The plurality of second joining areas 252 and the plurality of highly absorbent material fixing parts 253 are alternately arranged in the width direction of the second absorbent sheet 22a. In the example illustrated in FIGS. 2 and 5, three highly absorbent material fixing parts 253 are aligned and spaced from each other in the width direction of the second absorbent sheet 22a. The three highly absorbent material fixing parts 253 are arranged in approximately parallel with each other.

Each highly absorbent material fixing part 253 is a generally band-like (i.e., generally rectangular) area that extends linearly in the longitudinal direction of the second absorbent sheet 22a. That is, the plurality of highly absorbent material fixing parts 253 and the plurality of second joining areas 252 are arranged in generally stripe form. The highly absorbent material fixing parts 253 may have a greater width than the second joining areas 252. In each highly absorbent material fixing part 253, the second highly absorbent material 222*a* is fixed to at least one of the second upper sheet 221*a* and the second lower sheet 223*a* with an adhesive that is applied to at least one of the upper face of the second lower sheet 223*a* and the lower face of the second upper sheet 221*a*.

In the process of manufacturing the second absorbent sheet 22*a*, for example, this adhesive may be applied to the entire upper face of the second lower sheet 223*a* and the entire lower face of the second upper sheet 221*a*. In this case, the adhesive is present between the second upper sheet 221*a* and the second lower sheet 223*a* even in the second joining areas 252. However, the adhesive present between the second upper sheet 221*a* and the second lower sheet 223*a* is a small amount and therefore does not contribute much to the fixation of the second upper sheet 221*a* and the second lower sheet 223*a*. Thus, even in the case where the second joining areas 252 include the adhesive between the second upper sheet 221*a* and the second lower sheet 223*a*, the second upper sheet 221*a* and the second lower sheet 223*a* are fixed primarily by press bonding as described above.

In each second joining area 252, the second highly absorbent material 222*a* is substantially not present between the second upper sheet 221*a* and the second lower sheet 223*a*. In other words, in each second joining area 252, the second highly absorbent material 222*a* is not present at all between the second upper sheet 221*a* and the second lower sheet 223*a*, or it is present in slight density to such an extent that the second highly absorbent material 222*a* can be regarded as substantially not present, as compared with the second highly absorbent material 222*a* present in the highly absorbent material fixing part 253.

If the highly absorbent material fixing parts 253 and the second joining areas 252 described above are respectively referred to as "first regions" and "second regions," the second absorbent sheet 22*a* is also configured in the same manner as in the first absorbent sheet 22 such that a plurality of second regions and a plurality of first regions are alternately arranged in the width direction of the second absorbent sheet 22*a*. In each of the first regions, the second highly absorbent material 222*a* is fixed between the second upper sheet 221*a* and the second lower sheet 223*a*. In the second regions, the second highly absorbent material 222*a* is not present between the second upper sheet 221*a* and the second lower sheet 223*a*, and the second upper sheet 221*a* and the second lower sheet 223*a* are fixed directly to each other.

The amount of liquid absorbed per unit area of the first absorbent sheet 22 may be smaller than the amount of liquid absorbed per unit area of the second absorbent sheet 22*a*. In this case, the unit areas of the first absorbent sheet 22 and the second absorbent sheet 22*a* refer respectively to the unit areas of the first absorbent sheet 22 and the second absorbent sheet 22*a* in plan view. The amount of liquid absorbed per unit area of the first absorbent sheet 22 and the second absorbent sheet 22*a* refers to the amount of liquid absorbed per unit area of the highly absorbent material fixing parts 253 of the first absorbent sheet 22 and the second absorbent sheet 22*a* (i.e., a maximum amount of liquid absorbed). Alternatively, the amount of liquid absorbed per unit area of the first absorbent sheet 22 and the second absorbent sheet 22*a* may refer to an average amount of liquid absorbed per unit area of the first absorbent sheet 22 and the second absorbent sheet 22*a* as a whole.

The liquid absorption velocity of the second absorbent sheet 22*a* is higher than the liquid absorption velocity of the first absorbent sheet 22. The difference in liquid absorption velocity and the difference in the amount of liquid absorbed described above may be produced by, for example, differentiating the types of the first highly absorbent material 222 and the second highly absorbent material 222*a*. Alternatively, the difference in liquid absorption velocity and the difference in the amount of liquid absorbed may be produced by differentiating the amounts of the first highly absorbent material 222 and the second highly absorbent material 222*a* per unit area of the highly absorbent material fixing parts 253. For example, the first highly absorbent material 222 and the second highly absorbent material 222*a* may be made of the same type of material, and the weight of the first highly absorbent material 222 in the highly absorbent material fixing parts 253 of the first absorbent sheet 22 may be set to become smaller than the weight of the second highly absorbent material 222*a* in the highly absorbent material fixing parts 253 of the second absorbent sheet 22*a*.

As described above, the absorbent product 1 includes the liquid-pervious top sheet 21, the first absorbent sheet 22, the second absorbent sheet 22*a*, and the water-repellent or liquid-impervious back sheet 23. The first absorbent sheet 22 is disposed between the top sheet 21 and the back sheet 23. The second absorbent sheet 22*a* is disposed between the first absorbent sheet 22 and the back sheet 23. The first absorbent sheet 22 includes the first upper sheet 221, the first highly absorbent material 222 in particulate or fibrous form, and the first lower sheet 223. The first lower sheet 223 is disposed between the first upper sheet 221 and the back sheet 23. The first highly absorbent material 222 is fixed between the first upper sheet 221 and the first lower sheet 223.

The second absorbent sheet 22*a* includes the second upper sheet 221*a*, the second highly absorbent material 222*a* in particulate or fibrous form, and the second lower sheet 223*a*. The second lower sheet 223*a* is disposed between the second upper sheet 221*a* and the back sheet 23. The second highly absorbent material 222*a* is fixed between the second upper sheet 221*a* and the second lower sheet 223*a*.

On each longitudinal side, the first absorbent sheet 22 extends in the longitudinal direction beyond the longitudinal edge of the second absorbent sheet 22*a*. The extension 224 of the first absorbent sheet 22 beyond the second absorbent sheet 22*a* on each longitudinal side includes the back-sheet contact region 225 that is spaced in the longitudinal direction from the longitudinal edge of the second absorbent sheet 22*a* and that is in contact with the back sheet 23.

This configuration allows the liquid that is not immediately absorbed by the second absorbent sheet 22*a*, out of the liquid having passed through the first absorbent sheet 22 and reached the second absorbent sheet 22*a*, to be temporarily retained between the back-sheet contact region 225 of the first absorbent sheet 22 and the second absorbent sheet 22*a*. Thus, it is possible to reduce the possibility that the liquid that is not immediately absorbed by the second absorbent sheet 22*a* might pass through the first absorbent sheet 22 and return to the top sheet 21 (i.e., the return of liquid). As a result, it is possible to suppress the adhesion of the liquid such as urine having returned to the top sheet 21 to the wearer's skin.

As described above, on each longitudinal side of the first absorbent sheet 22, the distance D1 in the longitudinal direction between the back-sheet contact region 225 of the first absorbent sheet 22 and the edge of the second absorbent sheet 22*a* is greater than or equal to 2 mm and less than or equal to 20 mm. Also, the core end space 226 surrounded by the first absorbent sheet 22, the second absorbent sheet 22*a*, and the back sheet 23 is provided between the back-sheet contact region 225 and the above edge of the second absorbent sheet 22a. This configuration allows the liquid that is not immediately absorbed by the second absorbent sheet 22a, out of the liquid having passed through the first absorbent sheet 22 and reached the second absorbent sheet 22a, to be temporarily and readily retained in the core end space 226. As a result, the aforementioned return of liquid can be further suppressed.

In the absorbent product 1, the amount of liquid absorbed per unit area of the first absorbent sheet 22 is smaller than the amount of liquid absorbed per unit area of the second absorbent sheet 22a. Thus, the liquid having passed through the top sheet 21 immediately passes through the first absorbent sheet 22 and migrates away from the top sheet 21. The liquid having passed through the first absorbent sheet 22 is absorbed by the second highly absorbent material 222a of the second absorbent sheet 22a. This even further suppresses the return of liquid described above.

The first lower sheet 223 of the first absorbent sheet 22 is more pervious to liquids than the second lower sheet 223a of the second absorbent sheet 22a. Thus, the liquid having passed through the top sheet 21 immediately passes through the first absorbent sheet 22 and migrates away from the top sheet 21. The liquid having passed through the first absorbent sheet 22 remains in the second absorbent sheet 22a for some time and is then absorbed by the second highly absorbent material 222a. This further suppresses the return of liquid described above. Moreover, if the liquid absorption velocity of the second absorbent sheet 22a is set higher than the liquid absorption velocity of the first absorbent sheet 22, the liquid having passed through the first absorbent sheet 22 will be absorbed immediately by the second absorbent sheet 22a.

As described above, the first absorbent sheet 22 of the absorbent product 1 extends in the longitudinal direction beyond the longitudinal edge of the second absorbent sheet 22a on each longitudinal side. The first upper sheet 221 and the first lower sheet 223 are fixed to each other in the longitudinal edge portions of the first absorbent sheet 22.

This configuration prevents the first highly absorbent material 222 from escaping from the longitudinal ends of the first absorbent sheet 22. This configuration also reduces the thickness of the longitudinal end portions of the first absorbent sheet 22, thus improving the wearing comfort of the absorbent product 1. The configuration further reduces the possibility that the first highly absorbent material 222 having absorbed the liquid such as urine and swelled might leak out of the longitudinal ends of the first absorbent sheet 22. As a result, it is possible to suppress a decrease in the wearing comfort of the absorbent product 1 that has received the liquid such as urine.

As described above, the fixation of the first upper sheet 221 and the first lower sheet 223 in the longitudinal edge portions of the first absorbent sheet 22 is accomplished by press bonding. This allows the first upper sheet 221 and the first lower sheet 223 to be readily and securely fixed to each other in the first joining areas 251. The fixation of the first upper sheet 221 and the first lower sheet 223 is also accomplished by embossing. This allows the first upper sheet 221 and the first lower sheet 223 to be more securely fixed to each other in the first joining areas 251. The fixation of the first upper sheet 221 and the first lower sheet 223 is further accomplished by embossing that involves heating. This allows the first upper sheet 221 and the first lower sheet 223 to be yet more securely fixed to each other in the first joining areas 251.

In the first absorbent sheet 22, one of the first upper sheet 221 and the first lower sheet 223 has a higher content of heat-sealing fibers than the other sheet, and the first upper sheet 221 and the first lower sheet 223 are press-bonded by pressing this one sheet against the other sheet while heating the one sheet. This cause the heat-sealing fibers contained in the one sheet described above to be appropriately molten in the first joining areas 251, thus allowing the first upper sheet 221 and the first lower sheet 223 to be even more securely fixed to each other.

As described above, in the first absorbent sheet 22, the plurality of highly absorbent material fixing parts 253 are arranged in generally stripe form, and therefore it is possible to reduce the possibility that the first highly absorbent material 222, having absorbed the liquid such as urine from a wearer and swelled, might expand almost throughout the surface in the central part of the absorbent sheet 22, forming a gel block (i.e., a phenomenon in which following liquid such as urine is inhibited from penetrating into the absorbent sheet by the swelled highly absorbent material or the like and is accumulated on the highly absorbent material). As a result, it is possible to suppress the adhesion of the liquid such as urine, which has returned to the top sheet 21 due to the presence of the gel block, to the wearer's skin. In other words, the return of liquid due to a gel block can be suppressed. Similarly, in the second absorbent sheet 22a, the plurality of highly absorbent material fixing parts 253 are arranged in generally stripe form, and therefore it is possible to suppress the occurrence of a gel block.

In the absorbent product 1, the second upper sheet 221a and the second lower sheet 223a are not fixed to each other in the longitudinal edge portions of the second absorbent sheet 22a. This configuration simplifies the manufacture of the second absorbent sheet 22a. As a result, the cost of manufacture of the absorbent product 1 can be reduced. Although in the absorbent product 1, part of the second highly absorbent material 222a may escape from the longitudinal ends of the second absorbent sheet 22a, the second highly absorbent material 222a that has escaped from the second absorbent sheet 22a lies below the extensions 224 of the first absorbent sheet 22. This reduces the possibility that the wearer of the absorbent product 1 might feel the presence of the second highly absorbent material 222a having escaped via the top sheet 21. As a result, even if the second highly absorbent material 222a has escaped from the longitudinal ends of the second absorbent sheet 22a, it is possible to suppress a decrease in the wearing comfort of the absorbent product 1 due to indirect contact with the second highly absorbent material 222a.

As described above, in the absorbent product 1, the back-sheet contact region 225 of the first absorbent sheet 22 is fixed to the back sheet 23 on the longitudinal sides. This reduces the possibility that the second absorbent sheet 22a placed between the first absorbent sheet 22 and the back sheet 23 might be twisted or shifted in position relative to the first absorbent sheet 22. As a result, an immediate migration of the liquid from the first absorbent sheet 22 to the second absorbent sheet 22a is achieved. Also, even if the second highly absorbent material 222a has escaped from the longitudinal ends of the second absorbent sheet 22a as described above, it is possible to suppress a migration of the second highly absorbent material 222a from below the first absorbent sheet 22 to the area where the first absorbent sheet 22 is not present. As a result, a decrease in the wearing comfort of the absorbent product 1 is further suppressed.

In the absorbent product 1, the second upper sheet 221a of the second absorbent sheet 22a is fixed to the first lower sheet 223 of the first absorbent sheet 22. This configuration further reduces the possibility that the second absorbent sheet 22a might be twisted or shifted in position relative to the first absorbent sheet 22. As a result, an immediate migration of the liquid from the first absorbent sheet 22 to the second absorbent sheet 22a is achieved.

Figure 6:
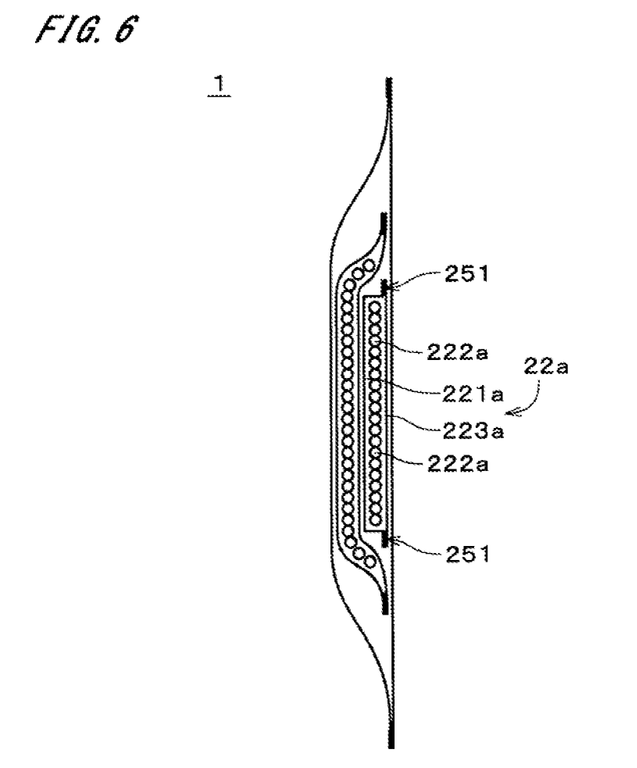
FIG. 6 is a sectional view of another absorbent product.
Figure 7:
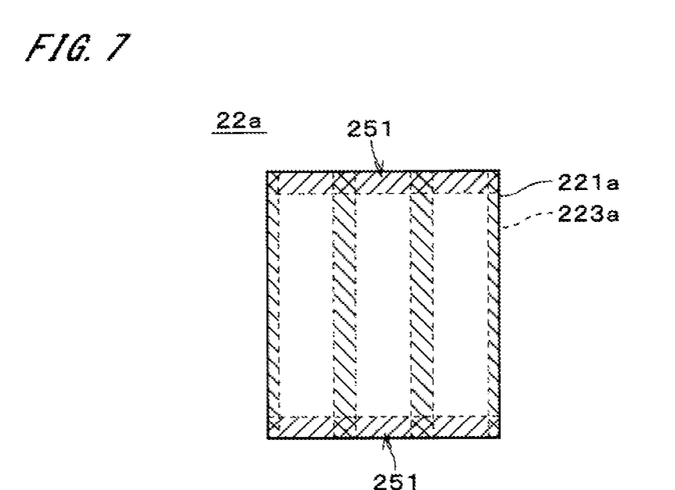
FIG. 7 is a plan view of the second absorbent sheet.

FIG. 6 is a sectional view illustrating another preferable example of the absorbent product 1. FIG. 6 is a sectional view of the absorbent product 1 perpendicular to the width direction and corresponds to FIG. 3. FIG. 7 is a plan view of the second absorbent sheet 22a of the absorbent product 1 illustrated in FIG. 6. In the example illustrated in FIGS. 6 and 7, the second upper sheet 221a and the second lower sheet 223a are bonded to each other in the longitudinal edge portions of the second absorbent sheet 22a, forming first joining areas 251. In each first joining area 251, the second upper sheet 221a and the second lower sheet 223a are fixed directly to each other.

Each first joining area 251 of the second absorbent sheet 22a is a generally rectangular area that is long in the width direction of the second absorbent sheet 22a. The longitudinal length of each first joining area 251 may, for example, be in the range of 5 to 50 mm. Each first joining area 251 is provided almost throughout the crosswise length of the second absorbent sheet 22a. The fixation of the second upper sheet 221a and the second lower sheet 223a in the first joining areas 251 may preferably be accomplished by press bonding. More preferably, the fixation of the second upper sheet 221a and the second lower sheet 223a in the first joining areas 251 is accomplished by press bonding by means of embossing. Yet more preferably, the fixation of the second upper sheet 221a and the second lower sheet 223a in the first joining areas 251 is accomplished by press bonding by means of embossing that involves heating.

In the example illustrated in FIGS. 6 and 7, the second upper sheet 221a and the second lower sheet 223a are fixed to each other in the longitudinal edge portions of the second absorbent sheet 22a. This configuration prevents the second highly absorbent material 222a from escaping from the longitudinal ends of the second absorbent sheet 22a. This configuration also reduces the thickness of the longitudinal ends of the second absorbent sheet 22a, thus improving the wearing comfort of the absorbent product 1. This configuration further reduces the possibility that second highly absorbent material 222a having absorbed the liquid such as urine and swelled might leak out of the longitudinal ends of the second absorbent sheet 22a.

As described above, the fixation of the second upper sheet 221a and the second lower sheet 223a in the longitudinal edge portions of the second absorbent sheet 22a is accomplished by press bonding. This allows the second upper sheet 221a and the second lower sheet 223a to be readily and securely fixed to each other in the first joining areas 251. The fixation of the second upper sheet 221a and the second lower sheet 223a is also accomplished by embossing. This allows the second upper sheet 221a and the second lower sheet 223a to be more securely fixed to each other in the first joining areas 251. Also, the fixation of the second upper sheet 221a and the second lower sheet 223a is accomplished by embossing that involves heating. This allows the second upper sheet 221a and the second lower sheet 223a to be yet more securely fixed to each other in the first joining areas 251.

Figure 8:
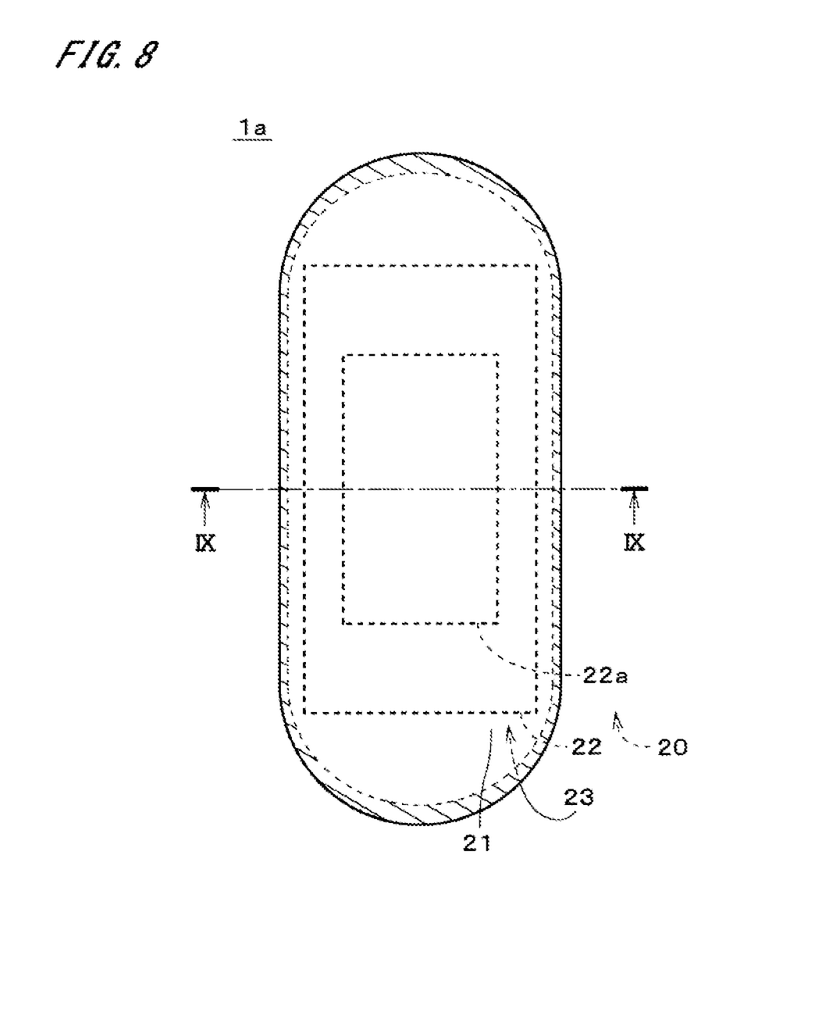
FIG. 8 is a plan view of an absorbent product according to a second embodiment.
Figure 9:
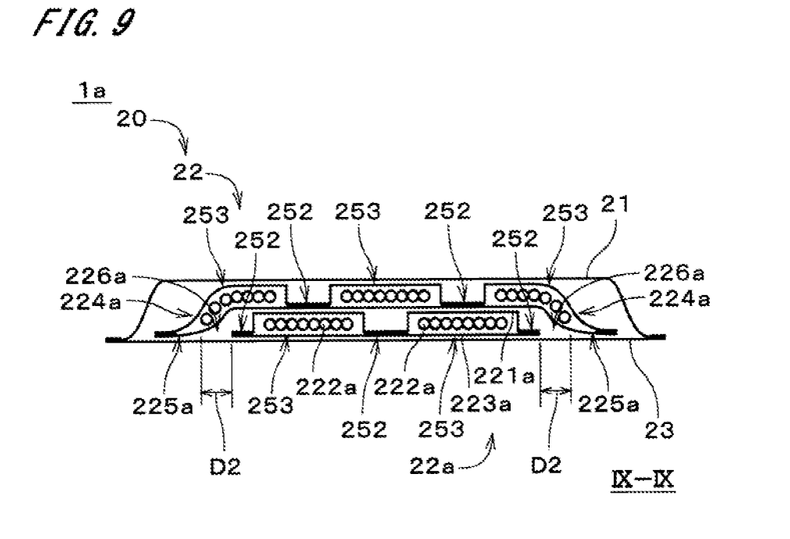
FIG. 9 is a sectional view of the absorbent product.
Figure 10:
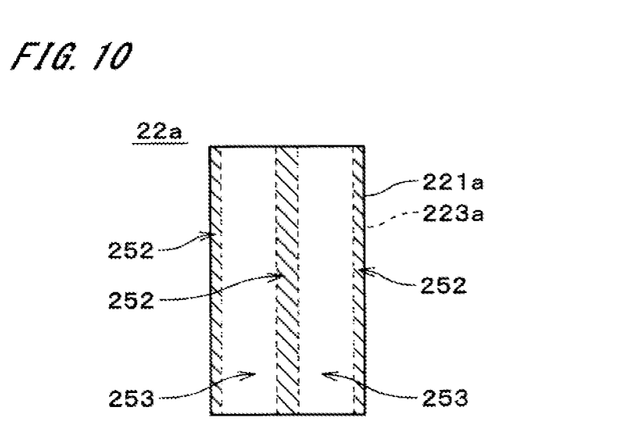
FIG. 10 is a plan view of the second absorbent sheet.

Next, an absorbent product 1a according to a second embodiment of the present invention will be described. FIG. 8 is a plan view of the absorbent product 1a. FIG. 9 is a sectional view of the absorbent product 1a taken at position IX-IX in FIG. 8 along a plane perpendicular to the longitudinal direction and corresponds to FIG. 2. FIG. 10 is a plan view of a second absorbent sheet 22a of the absorbent product 1a. The absorbent product 1a is approximately the same as the absorbent product 1 illustrated in FIGS. 1 to 3, except that the second absorbent sheet 22a has a smaller width than a first absorbent sheet 22. In the following description, constituent elements of the absorbent product 1a that correspond to those of the absorbent product 1 are given the same reference numerals.

As illustrated in FIGS. 8 and 9, the first absorbent sheet 22 extends in the width direction beyond edges in the width direction of the second absorbent sheet 22a on the sides in the width direction of the first absorbent sheet 22. On each side in the width direction, an extension 224a of the first absorbent sheet 22 beyond the second absorbent sheet 22a includes a lateral back-sheet contact region 225a that is spaced in the width direction from the edge in the width direction of the second absorbent sheet 22a and that is in contact with the back sheet 23. In other words, the edge in the width direction of the lateral back-sheet contact region 225a on the side closer to the second absorbent sheet 22a is spaced in the width direction from the edge in the width direction of the second absorbent sheet 22a. In yet other words, a non-contact region where the absorber 20 and the back sheet 23 are not in contact is present between the lateral back-sheet contact region 225a of the first absorbent sheet 22 and the edge in the width direction of the second absorbent sheet 22a.

The lateral back-sheet contact region 225a of the first absorbent sheet 22 is fixed to the back sheet 23 on both sides in the width direction of the first absorbent sheet 22. This reduces the possibility that the second absorbent sheet 22a placed between the first absorbent sheet 22 and the back sheet 23 might be twisted or shifted in position relative to the first absorbent sheet 22. As a result, an immediate migration of the liquid from the first absorbent sheet 22 and the second absorbent sheet 22a is achieved. The fixation of the lateral back-sheet contact region 225a and the back sheet 23 may be accomplished by bonding with a hot-melt adhesive. The fixation of the lateral back-sheet contact region 225a and the back sheet 23 may be accomplished using other various methods.

On each side in the width direction of the first absorbent sheet 22, a distance D2 in the width direction between the lateral back-sheet contact region 225a of the first absorbent sheet 22 and the edge in the width direction of the second absorbent sheet 22a may be greater than or equal to 2 mm and less than or equal to 20 mm. There is a space 226a surrounded by the first absorbent sheet 22, the second absorbent sheet 22a, and the back sheet 23 (hereinafter, referred to as a "lateral core end space 226a") between the lateral back-sheet contact region 225a and the edge in the width direction of the second absorbent sheet 22a. The lateral core end space 226a extends generally linearly in the longitudinal direction almost throughout the length of the second absorbent sheet 22a.

As illustrated in FIG. 10, in the second absorbent sheet 22a, the second upper sheet 221a and the second lower sheet 223a are not fixed to each other in the longitudinal edge portions. This simplifies the manufacture of the second absorbent sheet 22a. As a result, the cost of manufacture of the absorbent product 1a can be reduced.

As illustrated in FIGS. 9 and 10, three second joining areas 252 and two highly absorbent material fixing parts 253 are alternately arranged in the second absorbent sheet 22a. By arranging the plurality of highly absorbent material fixing parts 253 in generally stripe form in this way, it is possible to suppress the occurrence of a gel block in the second absorbent sheet 22a. As a result, the return of liquid due to a gel block can be suppressed. Each second joining area 252 of the second absorbent sheet 22a overlaps in the up-down direction with a highly absorbent material fixing part 253 of the first absorbent sheet 22. Two second joining areas 252 of the first absorbent sheet 22, excluding those on the side edges (i.e., in the edge portions in the width direction), overlap in the up-down direction with the highly absorbent material fixing parts 253 of the second absorbent sheet 22a. Thus, the highly absorbent material 222a of the second absorbent sheet 22a can immediately absorb the liquid that has passed through the first absorbent sheet 22.

In the absorbent product 1a illustrated in FIGS. 8 and 9, the first absorbent sheet 22 extends in the width direction beyond the edges in the width direction of the second absorbent sheet 22a on both sides in the width direction. On each side in the width direction, the extension 224a of the first absorbent sheet 22 beyond the second absorbent sheet 22a includes the lateral back-sheet contact region 225a that is spaced in the width direction from the edge in the width direction of the second absorbent sheet 22a and that is in contact with the back sheet 23.

This configuration allows the liquid that is not immediately absorbed by the second absorbent sheet 22a, out of the liquid having passed through the first absorbent sheet 22 and reached the second absorbent sheet 22a, to be temporarily retained between the lateral back-sheet contact region 225a of the first absorbent sheet 22 and the second absorbent sheet 22a. Thus, it is possible to reduce the possibility that the liquid that is not immediately absorbed by the second absorbent sheet 22a might pass through the first absorbent sheet 22 and return to the top sheet 21 (i.e., the return of liquid). As a result, it is possible to suppress the adhesion of the liquid such as urine having returned to the top sheet 21 to the wearer's skin.

As described above, on each side in the width direction of the first absorbent sheet 22, the distance D2 in the width direction between the lateral back-sheet contact region 225a of the first absorbent sheet 22 and the edge of the second absorbent sheet 22a is greater than or equal to 2 mm and less than or equal to 20 mm. Also, the lateral core end space 226a surrounded by the first absorbent sheet 22, the second absorbent sheet 22a, and the back sheet 23 is provided between the lateral back-sheet contact region 225a and the above edge of the second absorbent sheet 22a. This configuration allows the liquid that is not immediately absorbed by the second absorbent sheet 22a, out of the liquid having passed through the first absorbent sheet 22 and reached the second absorbent sheet 22a, to be temporarily and readily retained in the lateral core end space 226a. As a result, the aforementioned return of liquid can be further suppressed.

The absorbent products 1 and 1a described above may be modified in various ways.

For example, in the first absorbent sheet 22 of the absorbent products 1 and 1a, the fixation of the first upper sheet 221 and the second upper sheet 221a in the first joining areas 251 may be accomplished by embossing that does not involve heating, or may be accomplished by press bonding by means other than embossing (e.g., heat sealing or ultrasonic sealing), or may be accomplished using various methods other than press bonding. The same applies to the fixation of the first upper sheet 221 and the first lower sheet 223 in the second joining areas 252 of the first absorbent sheet 22. The same also applies to the fixation of the second upper sheet 221a and the second lower sheet 223a in the second joining areas 252 of the second absorbent sheet 22a. In the case where the first joining areas 251 are provided in the longitudinal edge portions of the second absorbent sheet 22a as illustrated in FIGS. 6 and 7, the same also applies to the fixation of the second upper sheet 221a and the second lower sheet 223a in the first joining areas 251.

In the absorbent products 1 and 1a, the first absorbent sheet 22 does not necessarily have to be provided with the first joining areas 251, and the first upper sheet 221 and the first lower sheet 223 may not be fixed to each other in the longitudinal edge portions of the first absorbent sheet 22. That is, the first upper sheet 221 and the first lower sheet 223 in the longitudinal edge portions of the first absorbent sheet 22 may not be fixed to each other in the area excluding the second joining areas 252, or may not be fixed to each other throughout the width.

In the absorbent products 1 and 1a, the second upper sheet 221a of the second absorbent sheet 22a and the first lower sheet 223 of the first absorbent sheet 22 may not be fixed to each other. In this case, a more immediate migration of the liquid such as urine from the first absorbent sheet 22 to the second absorbent sheet 22a is possible than in the case where the adhesive or the like is present between the first absorbent sheet 22 and the second absorbent sheet 22a.

In the absorbent products 1 and 1a, the back-sheet contact region 225 provided in the extension 224 of the first absorbent sheet 22 beyond the second absorbent sheet 22a may not be fixed to the back sheet 23. With techniques associated with the present invention, the back-sheet contact region 225 may be in contact with the edges in the longitudinal direction of the second absorbent sheet 22a.

In the absorbent product 1a, the lateral back-sheet contact region 225a provided in the extension 224a of the first absorbent sheet 22 beyond the second absorbent sheet 22a may not be fixed to the back sheet 23. Also, the lateral back-sheet contact region 225a may be in contact with the edge in the width direction of the second absorbent sheet 22a.

Although the plurality of highly absorbent material fixing parts 253 of the first absorbent sheet 22 are arranged in generally stripe form, the arrangement of the highly absorbent material fixing parts 253 and the shape of each highly absorbent material fixing part 253 may be modified in various ways. For example, a plurality of highly absorbent material fixing parts 253 having a generally circular shape in plan view may be arranged in a matrix. As another alternative, the highly absorbent material 222 may be arranged throughout the region of the first absorbent sheet 22, excluding the edge portions in the width direction. The same applies to the second absorbent sheet 22a.

The shape of the absorbent products 1 and 1a in plan view may be modified in various ways. For example, the shape of the absorbent products 1 and 1a in plan view may be a generally hourglass shape whose width in the longitudinal ends is greater than the width in the longitudinal center portion.

The configurations of the above-described preferred embodiments and variations may be appropriately combined as long as there are no mutual inconsistencies.

While the invention has been shown and described in detail, the foregoing description is in all aspects illustrative and not restrictive. It is therefore to be understood that numerous modifications and variations can be devised without departing from the scope of the invention.

REFERENCE SIGNS LIST 1, 1a Absorbent product
20 Absorbent core

21 Top sheet
22 First absorbent sheet
22a Second absorbent sheet
23 Back sheet
221 First upper sheet
221a Second upper sheet
222 First highly absorbent material
222a Second highly absorbent material
223 First lower sheet
223a Second lower sheet
224, 224a Extension
225 Back-sheet contact region
225a Lateral back-sheet contact region
226 Core end space
226a Lateral core end space
251 First joining area

The invention claimed is:

1. An absorbent product for receiving body wastes from a wearer, comprising:
   a liquid-pervious top sheet;
   a liquid-repellent or liquid-impervious back sheet;
   a first absorbent sheet disposed between said top sheet and said back sheet; and
   a second absorbent sheet disposed between said first absorbent sheet and said back sheet,
   said first absorbent sheet including:
   a first upper sheet;
   a first lower sheet disposed between said first upper sheet and said back sheet; and
   a first highly absorbent material in particulate or fibrous form that is fixed between said first upper sheet and said first lower sheet,
   said second absorbent sheet including:
   a second upper sheet;
   a second lower sheet disposed between said second upper sheet and said back sheet; and
   a second highly absorbent material in particulate or fibrous form that is fixed between said second upper sheet and said second lower sheet,
   wherein, on each side in a longitudinal direction, said first absorbent sheet extends in said longitudinal direction beyond an edge in said longitudinal direction of said second absorbent sheet, and the extension of said first absorbent sheet beyond said second absorbent sheet includes a back-sheet contact region that is spaced in said longitudinal direction from said edge of said second absorbent sheet and that is in contact with said back sheet,
   wherein said second upper sheet and said second lower sheet are not fixed to each other in each edge portion in said longitudinal direction of said second absorbent sheet.

2. The absorbent product according to claim 1, wherein on each side in said longitudinal direction, a distance in said longitudinal direction between said back-sheet contact region of said first absorbent sheet and said edge of said second absorbent sheet is greater than or equal to 2 mm and less than or equal to 20 mm, and a space surrounded by said first absorbent sheet, said second absorbent sheet, and said back sheet is provided between said back-sheet contact region and said edge of said second absorbent sheet.

3. The absorbent product according to claim 1, wherein an amount of liquid absorbed per unit area of said first absorbent sheet is smaller than an amount of liquid absorbed per unit area of said second absorbent sheet.

4. The absorbent product according to claim 1, wherein on each side in said longitudinal direction, said back-sheet contact region of said first absorbent sheet is fixed to said back sheet.

5. The absorbent product according to claim 1, wherein said second upper sheet of said second absorbent sheet is fixed to said first lower sheet of said first absorbent sheet.

6. The absorbent product according to claim 1, wherein said first lower sheet is more pervious to liquid than said second lower sheet.

7. The absorbent product according to claim 1, wherein on each side in a width direction, said first absorbent sheet extends in said width direction beyond a side edge in said width direction of said second absorbent sheet, and the extension of said first absorbent sheet beyond said second absorbent sheet includes a lateral back-sheet contact region that is spaced in said width direction from said side edge in said width direction of said second absorbent sheet and that is in contact with said back sheet.

8. The absorbent product according to claim 1, wherein said first upper sheet and said first lower sheet are fixed to each other in each edge portion in said longitudinal direction of said first absorbent sheet.

9. The absorbent product according to claim 8, wherein the fixation of said first upper sheet and said first lower sheet is accomplished by embossing.

10. The absorbent product according to claim 9, wherein the fixation of said first upper sheet and said first lower sheet is accomplished by embossing that involves heating.

* * * * *